United States Patent [19]

Rodson et al.

[11] 4,456,569
[45] Jun. 26, 1984

[54] ENCAPSULATION PROCESS

[75] Inventors: Marius Rodson, El Cerrito; Herbert B. Scher, Moraga, both of Calif.

[73] Assignee: Stauffer Chemical Company, Westport, Conn.

[21] Appl. No.: 556,670

[22] Filed: Nov. 30, 1983

Related U.S. Application Data

[62] Division of Ser. No. 383,448, Jun. 1, 1982.

[51] Int. Cl.$^3$ .............................................. B29C 13/00
[52] U.S. Cl. ........................................ 264/4.7; 427/3; 427/222; 525/58; 525/66; 528/48
[58] Field of Search ...................... 264/4.7; 427/3, 222; 525/58, 66; 528/48

[56] References Cited

U.S. PATENT DOCUMENTS

| | | | |
|---|---|---|---|
| 1,696,374 | 12/1928 | Agthe | 260/23 |
| 1,754,651 | 4/1930 | Schidrowitz | 260/112 |
| 2,047,398 | 7/1936 | Voss et al. | 260/2 |
| 2,609,350 | 9/1952 | Spatt | 525/57 |
| 2,677,672 | 5/1954 | Luce | 260/29.6 |
| 2,699,392 | 1/1955 | Herrick, Jr. et al. | 95/7 |
| 2,725,308 | 11/1955 | Nickerson | 117/65 |
| 2,744,835 | 5/1956 | Caroselli | 117/72 |
| 2,866,772 | 12/1958 | Sellers | 260/45.5 |
| 3,428,588 | 2/1969 | Skouldchi et al. | 260/23 |
| 3,475,515 | 10/1969 | Blatz et al. | 260/875 |
| 3,492,254 | 1/1970 | Strund et al. | 260/17 |
| 4,046,741 | 9/1977 | Scher | 528/490 |
| 4,119,463 | 10/1978 | Iguchi et al. | 96/67 |
| 4,285,720 | 8/1981 | Scher | 71/88 |

*Primary Examiner*—J. Ziegler
*Attorney, Agent, or Firm*—Leona L. Lauder

[57] ABSTRACT

A protective colloid for use in an interfacial polymerization process comprising a graft copolymer of polyvinyl alcohol and methyl vinyl ether/maleic acid.

3 Claims, No Drawings

ENCAPSULATION PROCESS

This is a divisional of application Ser. No. 383,448, filed June 1, 1982.

FIELD OF THE INVENTION

This invention relates to an interfacial polymerization process and, in particular, to an improved protective colloid for use in such a process.

BACKGROUND OF THE INVENTION

The use of membranes, coatings and capsules for the controlled release of liquid materials is well known in the art of both agricultural and non-agricultural chemicals. In agriculture, controlled release techniques have improved the efficiency of herbicides, insecticides, fungicides, bactericides, and fertilizers. Non-agricultural uses include encapsulated dyes, inks, pharmaceuticals, flavoring agents, and fragrances.

The most common forms of controlled-release materials are coated droplets or microcapsules, coated solids including both porous and non-porous particles, and coated aggregates of solid particles. In some instances, the coating is porous and the entrapped material is released to the surrounding medium at a slow rate by diffusion through the pores. In other instances, the encapsulating film is water-soluble and the encapsulated material is released when the capsule is placed in contact with water. Still other coatings release the entrapped material when the coating is ruptured by external force.

This invention relates to porous coatings. In addition to providing controlled release, these coatings facilitate the dispersion of water-immiscible liquids into water and water-containing media, such as wet soil. Droplets encapsulated in this manner are particularly useful in agriculture, where water from irrigation, rain, and water sprays is frequently present. A variety of processes for producing such capsules is known.

Interfacial polymerization is one type of process for producing these capsules. Typically, interfacial polymerization involves preparation of two distinct phases. One of the film-forming reactants is dissolved in an aqueous phase and the other reactant is dissolved in a hydrophobic phase. Reaction between the two film-forming reactants occurs at the phase interface when the phases are placed in contact with each other.

A second type of interfacial polymerization process is disclosed in U.S. Pat. Nos. 4,046,741 (Scher, Sept. 6, 1977) and in copending application Ser. No. 922,473, now U.S. Pat. No. 4,285,720. Applicant's process differs from typical interfacial polymerization processes in that one of the film-forming reactants is formed in situ. Material to be encapsulated and at least one polyisocyanate are present in an organic phase. A surfactant and a protective colloid are present in an aqueous phase. After dispersion of the organic phase into the aqueous phase and heating, the isocyanate monomers react with water at the phase interface to form an amine. This amine then reacts with remaining isocyanate monomers to form a polyureamicrocapsule wall which encapsulates the "material to be encapsulated." The product of this process is a formulation and includes the microcapsules dispersed in water.

The purpose of the protective colloid which is present in the aqueous phase of Applicant's process is to prevent recombination of particles during the wall formation step. Among the protective colloids previously disclosed are polyacrylates, methylcellulose, polyvinyl alcohol, polyacrylamide and poly(methylvinyl ether/maleic anhyride).

Pesticide loading refers to the amount of pesticide present in a given quantity of formulation. The maximum pesticide loading which can be achieved using any one of the previously disclosed protective colloids is about 2.5 pounds (1b) of pesticide/gallon (gal) of formulation. Above that level, recombination, foaming or gellation may become a problem.

SUMMARY OF THE INVENTION

It has now been discovered that a graft copolymer of polyvinyl alcohol and methyl vinyl ether/maleic acid has properties as a protective colloid for Applicant's microencapsulation system far superior to any protective colloids previously described. This graft protective colloid has excellent protective action. No recombination of particles during formation of the microcapsule wall occurred even at a pesticide loading of 4 lb of pesticide/gal of microcapsule formulation. This is about 1.5 lb/gal (a 60% increase) greater than anything previously achieved. In addition, foaming due to escaping carbon dioxide gas can easily be controlled and gellation was not a problem.

A graft copolymer of polyvinyl alcohol and poly (methylvinyl ether/maleic anhydride) is known in the prior art. For example, U.S. Pat. No. 2,609,350 (Spatt, Dec. 21, 1946) discloses such a copolymer for use as an impregnating composition to impart a permanent finish to textiles.

DETAILED DESCRIPTION OF THE INVENTION

This invention relates to use of a graft copolymer of polyvinyl alcohol and methylvinyl ether/maleic acid (hydrolyzed methylvinyl ether/maleic anhydride) as a protective colloid in a process for forming microcapsules by interfacial polymerization. A process in which the present invention is particularly useful is described in copending application Ser. No. 922,473 and may be briefly summarized as follows:

Material to be encapsulated and at least one polyisocyanate are present in an organic phase. Examples of pesticides suitable as material to be encapsulated include the following:

HERBICIDES

S-ethyl-N-cyclohexyl-N-ethylthiocarbamate (cycloate)
S-ethyl hexahydro-1H-azepine-1-carbothioate (molinate)
S-2,3-dichloroallyl di-isopropylthiocarbamate (diallate)
S-2,3-trichloroallyl di-isopropylthiocarbamate (triallate)
S-ethyl dipropylthiocarbamate (EPTO)
S-4-chlorobenzyl diethylthiocarbamate (benthiocarb)
S-ethyl diisobutylthiocarbamate (butylate)
S-benzyl di-sec-butylthiocarbamate
S-propyl dipropylthiocarbamate (vernolate)
S-propyl butylethylthiocarbamate (pebulate)
N,N-diallylchloroacetamide (allidochlor)
α-chloro-6'-ethyl-N-(2-methoxy-1-methylethyl)-acetanilide (metolachlor)
N-butoxymethyl-α-chloro-2',6'-diethylacetanilide (butachlor)

S-(O,O-diisopropyl phosphorodithioate) ester of N-(2-mercaptoethyl)benzenesulfonamide (bensulide)
N-benzyl-N-isopropyltrimethylacetamide (butam)
2-chloroallyl diethyldithiocarbamate (CDEC)
2-sec-butyl-4,6-dinitrophenol (dinoseb)
2,6-dinitro-N,N-dipropylcumidine (isopropalin)
N-(cyclopropylmethyl)-α,α-trifluoro-2,6-dinitro-N-propyl-p-toluidine (profluralin)
2-(1,2-dimethylpropylamino)-4-ethylamino-6-methylthio-1,3,5-triazine (dimethametryn)
2-ethyl-5-methyl-5-(2-methylbenzyloxy)-1,3-dioxane

INSECTICIDES

S-tert-butylthiomethyl O,O-diethyl phosphorodithioate (terbufos)
O,O-diethyl-O-4-methylsulphinylphenyl phosphorothioate (fensulfothion)
O,O-diethyl O-2-isopropyl-6-methylpyrimidin-4-yl phosphorothioate (diazinon)
O,O-diethyl S-2-ethylthioethyl phosphorodithioate (disulfoton)
S-chloromethyl O,O-diethyl phosphorodithioate (chlormephos)
O-ethyl S,S-dipropyl phosphorodithioate (ethoprophos)
O,O-diethyl S-ethylthiomethyl phosphorodithioate (phorate)
O-(4-bromo-2-chlorophenyl) O-ethyl S-propyl phosphorodithioate (prophenofos)
S-1,2-di(ethoxycarbonyl)ethyl O,O-dimethyl phosphorodithioate (malathion)
O,O,O',O'-tetraethyl S,S'-methylene di(phosphorodithioate) (ethion)
O-(4-bromo-2,5-dichlorophenyl) O,O-diethyl phosphorothioate (bromophos-ethyl)
S-4-chlorophenylthiomethyl O,O-diethyl phosphorodithioate (carbophenothion)
2-chloro-1-(2,4-dichlorophenyl)vinyl diethyl phosphate (chlorphenvinphos)
O-2,5-dichloro-4-(methylthio)phenyl O,O-diethyl phosphorodithioate (chlorthiophos)
O-4-cyanophenyl O,O-dimethyl phosphorothioate (cyanophos)
O,O-dimethyl O-2-methylthioethyl phosphorothioate (demephion)
O,O-diethyl O-2-ethylthioethyl phosphorothioate (demeton)
O-2,4-dichlorophenyl O,O-diethyl phosphorothioate (dichlorofenthion)
O-2,4-dichlorophenyl O-ethyl phenylphosphonothioate (EPBP)
O,O-diethyl O-5-phenylixoxazol-3-yl phosphorothioate (isoxathion)
1,3-di(methoxycarbonyl)-1-propen-2-yl dimethyl phosphate
S,S'-(1,4-dioxane-2,3-diyl) O,O,O'O'-tetraethyl di(phosphorodithioate) (dioxathion)
O,O-dimethyl-O-4-nitro-m-tolyl phosphorothioate (fenitrothion)
O,O-dimethyl O-4-methylthio-m-tolyl phosphorothioate (fenthion)
O-(5-chloro-1-isopropyl-1,2,4-triazol-3-yl) O,O-diethyl phosphorothioate (isazophos)
S-2-isopropylthioethyl O,O-dimethyl phosphorodithioate (isothioate)
4-(methylthio)phenyl dipropyl phosphate (propaphos)
1,2-dibromo-2,2-dichloroethyl dimethyl phosphate (naled)
O,O-diethyl α-cyanobenzyldeneamino-oxyphosphonothioate (phoxim)
O,O-diethyl O-4-nitrophenyl phosphorothioate (parathion)
O-2-diethylamino-6-methylpyrimidin-4-yl O,O-diethyl phosphorothioate (pirimiphos-ethyl)
O-2-diethylamino-6-methylpyrimidin-4-yl O,O-dimethyl phosphorothioate (pirimiphos-methyl)
(E)-O-2-isopropoxycarbonyl-1-methylvinyl O-methyl ethylphosphoramidothioate (propetamphos)
O,O,O',O'-tetraethyldithiopyrophosphate (sulfotep)
O,O,O',O'-tetramethyl O,O'-thiodi-p-phenylene diphosphorothioate (temephos)
S-2-ethylthioethyl O,O-dimethyl phosphorodithioate (thiometon)
O,O-diethyl O-1-phenyl-1,2,4-triazol-3-yl phosphorothioate (triazophos)
O-ethyl O-2,4,5-trichlorophenyl ethylphosphonothioate (trichloronate)
(±)-3-allyl-2-methyl-4-oxocyclopent-2-enyl (±)-cis,-trans-chrysanthemate (allethrin)
(±)-3-allyl-2-methyl-4-oxocyclopent-2-enyl (±)-trans-chrysanthemate (bioallethrin)
3-phenoxybenzyl (±)-cis,trans-chrysanthemate (phenothrin) pyrethrins
2-(2-butoxyethoxy)ethyl thiocyanate
isobornyl thiocyanoacetate (terpinyl thiocyanoacetate)
carbon disulfide
2-(4-tert-butylphenoxy)cyclohexyl prop-2-ynyl sulphite (propargite)
4,6-dinitro-6-octylphenyl crotonates (dinocap)
ethyl 4,4'-dichlorobenzilate (chlorobenzilate)

DEFOLIANTS

S,S,S-tributyl phosphorothioate
tributyl phosphorotrithioite (merphos)

FUNGICIDES copper naphthenates
5-ethoxy-3-trichloromethyl-1,2,4-thiadiazole (etridiazole)
O-ethyl S,S-diphenyl phosphorodithioate (edifenphos)

INSECT REPELLENTS 6-butoxycarbonyl-2,3-dihydro-2,2-dimethylpyran-4-one (butopyronoxyl)
N,N-diethyl-m-toluamide (deet)
dibutyl phthalate
dibutyl succinate
1,5a,6,9,9a,9b-hexahydro-4a(4H)-dibenzofurancarboxaldehyde
dipropyl pyridine-2,5-dicarboxylate The polyisocyanate, which is also present in the organic phase, reacts with water to form an amine. This amine then reacts with additional isocyanate monomers to form a polyurea capsule wall. Suitable polyisocyanates include aromatic diisocyanate, aliphatic diisocyanate, high molecular weight linear aliphatic diisocyanates, isocyanate prepolymers and combinations thereof. It is important, for purposes of the present invention, that the capsular wall be formed from polyisocyanates or a combination of polyisocyanates with other monomers.

A surfactant and a protective colloid are present in an aqueous phase. The purpose of the surfactant is to lower the surface tension of the fluid interface when the aqueous phase is brought into contact with the organic phase. Examples of suitable surfactants include sodium isopropyl naphthalene sulfonate, polyoxyethylenesorbitol oleate laurate, ethoxylated nonylphenols and polyethylene glycol ethers of linear alcohols.

The protective colloid stabilizes the system against aggregation, flocculation and coalescense when the organic phase is dispersed into the aqueous phase. The present invention relates to an improved protective colloid for use in an interfacial polymerization system such as the one being described. Prior art protective colloids include polyacrylates, methyl cellulose, polyvinyl alcohol, polyacrylamide and poly(methylvinyl ether/maleic anhydride).

To form the microcapsule wall, the organic phase is dispersed into the aqueous phase. Reaction of the polyisocyanate with water to form an amine and subsequent reaction of this amine with additional isocyanate to form a polyurea wall is accomplished by appropriate adjustment of temperature and pH.

The present invention comprises the use of an improved protective colloid in the process described. This improved protective colloid is a graft copolymer of polyvinyl alcohol and hydrolyzed methylvinyl ether/maleic anhydride.

The optimum weight ratio of hydrolyzed methylvinyl ether/maleic anhydride (Gantrez ® AN119 (MW=250,000)) to polyvinyl alcohol (Vinol ® 205 (MW=10,000)) for the preparation of the graft protective colloid is 30/1. This represents a molecular ratio of 1/1. Weight ratios about 30/1 are optimum. Higher ratios are not as effective in preventing recombination and lower ratios may cause foam problems. However, weight ratios within the broad range of 300:1 hydrolyzed methylvinyl ether/maleic anhydride:polyvinyl alcohol to 10:1 hydrolyzed methylvinyl ether/maleic anhydride:polyvinyl alcohol may be used depending on other reaction conditions.

The graft protective colloid may be prepared by varying methods as illustrated by the following examples.

EXAMPLE I

Twenty-nine grams (29 g) of Gantrez ® AN119 (General Aniline and Film Corp.) were dispersed in 266.0 g of water at room temperature (25° C.). Five g of a 20% aqueous solution of Vinol ® (Air Products and Chemicals, Inc.) were blended in. The slurry was warmed to 70° C. and stirring was maintained for 2 hours. The resulting solution was hazy and viscous.

EXAMPLE II

Seventy-nine and two-tenths g of Gantrez ® AN119 and 0.88 g of Vinol ® 205 were dispersed in 320 g of water at 40° C. The slurry was warmed up to 70° C. with stirring. These conditions were maintained for 2 hours, resulting in hazy viscous fluid.

EXAMPLE III

Thirty-eight g of Gantrez ® AN119 and 1.9 g of Vinol ® 205 were dispersed in 360 g of water at room temperature. The slurry was warmed to 95° C. and stirring at this temperature was maintained for 2 hours, resulting in formation of a hazy, viscous fluid.

EXAMPLE IV

Eighteen and two-tenths g of Gantrez ® AN119 and 1.82 g of Vinol ® 205 were dispersed in water at room temperature. Stirring was maintained for 24 hours, resulting in the formation of a hazy fluid.

Physically, there is evidence for the formation of a Vinol ® 205/Gantrez ® An119 graft protective colloid by the methods described. The resulting solution is turbid whereas the individual solutions of Vinol ® 205 and Gantrez ® AN119 and mixtures thereof are clear.

Use of Protective Colloid

The graft protective colloid is initially present in the aqueous phase of an interfacially polymerizable system. Its purpose is to prevent the recombination of particles during the wall formation step. The following are examples of how the graft protective colloid is used:

EXAMPLE V-VIII

Preparation of the organic phase, aqueous phase, and the microcapsule wall was the same in each of these examples.

An organic phase, comprising 340.4 g of S-ethyl N,N-diisobutylthiolcarbamate (material to be encapsulated), 15.2 g of polymethylenepolyphenyl isocyanate and 12.5 g of toluene diisocyanate was prepared. An aqueous phase, comprising 56.2 g of a 10% colloid graft solution, 4.2 g of a 20% aqueous solution of Tergitol ® 15-S-7 (Union Carbide) and 220.6 g of water was prepared. The organic phase was dispersed into the aqueous phase and heated to form the microcapsule wall.

The ratio of Gantrez ® AN119:Vinol ® 205 varied for each example. The following table shows the ratios used and the observed results.

| Example No. | Ratio Gantrez ® AN119:Vinol ® 205 In Graft Polymer | Results |
|---|---|---|
| V | 3.33:1 | no recombination |
| VI | 10:1 | no recombination |
| VII | 28.5:1 | no recombination |
| VIII | 100:1 | recombination of particles after heating at 50° C. for 10 minutes |

The results shown for Examples IV–VIII, in particular, may be contrasted with the following example in which a simple polymer mixture was used in place of a graft protective colloid.

EXAMPLE IX

An organic phase was prepared as in the previous examples. An aqueous phase comprising 50.6 g of a 10% aqueous Gantrez ® AN119 solution, 2.8 g of a 20% aqueous Vinol ® 205 solution (ratio of Gantrex ® AN119:Vinol ® 205 is 10:1), 4.2 g of a 20% aqueous Tergitol ® 15-S-7 solution and 223.4 g of water was prepared. The organic phase was dispersed into the aqueous phase and heated to form the microcapsule wall. Severe recombination of particles occurred on reaching 50° C.

What is claimed is:

1. In an interfacial polymerization process characterized by the steps of:
   (a) combining a material to be encapsulated and at least one polyisocyanate in an organic phase;
   (b) incorporating a surfactant and a protective colloid in an aqueous phase;
   (c) dispersing the organic phase into the aqueous phase; and (d) forming a polyurea-microcapsule wall at the phase interface, the improvement which comprises, using a protective colloid comprising a graft copolymer of polyvinyl alcohol and methyl vinyl ether/maleic acid.

2. In an interfacial polymerization process as defined in claim 1, further characterized by forming the polyurea microcapsule wall from polyisocyanates or a combination of polyisocyanates and other monomers, the improvement which comprises using a protective colloid comprising a graft copolymer of polyvinyl alcohol and methyl vinyl ether/maleic acid.

3. In an interfacial polymerization process as defined in claim 1, wherein the improvement further comprises using the protective colloid in a weight ratio in the range of about 1:10 to about 1:300 polyvinyl alcohol to methyl vinyl ether/maleic acid.

* * * * *